United States Patent [19]

Nakanishi et al.

[11] Patent Number: 4,950,781

[45] Date of Patent: Aug. 21, 1990

[54] PREPARATION PROCESS FOR AROMATIC HYDROXYCARBOXYLIC ACID

[75] Inventors: Takehisa Nakanishi; Toshizumi Miura, both of Takaishi; Masao Hashimoto, Yokohama, all of Japan

[73] Assignee: Mitsui Toatsu Chemicals, Inc., Tokyo, Japan

[21] Appl. No.: 439,701

[22] Filed: Nov. 21, 1989

[30] Foreign Application Priority Data

Nov. 29, 1988 [JP] Japan .................. 63-299627

[51] Int. Cl.$^5$ ............................................. C07C 51/15
[52] U.S. Cl. ................................................... 562/424
[58] Field of Search ......................................... 562/424

[56] References Cited

FOREIGN PATENT DOCUMENTS 212523  9/1986  Japan .

*Primary Examiner*—Paul J. Killos
*Attorney, Agent, or Firm*—Burns, Doane, Swecker & Mathis

[57] ABSTRACT

A process for the preparation of aromatic hydroxycarboxylic acids by reacting alkali metal salts of phenol with carbon dioxide in organic phosphine oxides containing straight or branched alkyl groups having from 1 to 8 carbon atoms and phenyl groups.

12 Claims, No Drawings

PREPARATION PROCESS FOR AROMATIC HYDROXYCARBOXYLIC ACID

Background of the Invention

1. Field of the Invention

The present invention relates to a process for the preparation of an aromatic hydroxycarboxylic acid and more particularly to a process for preparing an aromatic hydroxycarboxylic acid having a high content of p-hydroxybenzoic acid.

2. Prior Art of the Invention

The Kolbe Schmitt reaction has been known as a solventless process for reacting metal salts of phenols with carbon dioxide at high temperatures under increased pressure. In the reaction, carbon dioxide is absorbed in anhydrous sodium phenolate and heated to 120 to 140° C. to form monosodium salicylate and disodium salicylate. On the other hand, when potassium phenolate is heated at high temperatures, p-hydroxybenzoic acid is a main product and salicylic acid is a by-product [Handbook of Organic Chemistry, p454 (Published from Gihodo,Tokyo) ].

As to a process using a solvent, Hirao et al have reported on the reaction in various solvents including protic solvents such as tert-butanol; aprotic solvents such as toluene, diphenyl ether, N,N-dimethylformamide and dimethylsulfoxide; and high boiling solvents such as kerosene and light oil [Journal of Organic Synthesis Society, 26,992(1967) and 27, 648(1968) ].

Summary of the Invention

The object of the present invention is to provide a process for the preparation of an aromatic hydroxycarboxylic acid having a high content of p-hydroxybenzoic acid by reacting an alkali metal salt of phenol with carbon dioxide in the presence of a specific solvent.

The present inventors have carried out an intensive investigation in order to achieve the above object. As a result, they have found that a carboxyl group can selectively substitute on the para-position of a hydroxyl group by conducting carboxylation reaction in an organic phosphine oxide solvent. Thus the invention has been completed.

One aspect of the present invention is a process for the preparation of an aromatic hydroxycarboxylic acid comprising reacting an alkali metal salt of phenol with carbon dioxide in a solvent containing at least one organic phosphine oxide represented by the formula (I):

wherein $R^1$, $R^2$ and $R^3$ are a straight or branched alkyl group having from 1 to 8 carbon atoms or a phenyl group and may be same or different from each other.

The aromatic hydroxycarboxylic acid obtained by the process of the present invention is a compound useful as an antiseptic, an intermediate for agricultural chemicals and medicines, and a material for various aromatic polyester resins.

According to the process of the present invention p-hydroxybenzoic acid can be obtained in high selectivity by reacting the alkali metal salt of phenol in an organic phosphine oxide solvent.

Consequently, the process of the present invention is economically advantageous and industrially very valuable.

Detailed Description of the Invention

The organic phosphine oxide used in the process of the present invention is represented by the formula (I):

wherein $R^1$, $R^2$ and $R^3$ are a straight or branched alkyl group having from 1 to 8 carbon atoms or a phenyl group and may be same or different from each other.

Exemplary phosphine oxides which may be used include, for example, trimethylphosphine oxide, triethylphosphine oxide, tri-n-propylphosphine oxide, triisOpropylphosphine oxide, tri-sec-butylphosphine oxide, tri-n-butylphosphine oxide, tri-hexylphosphine oxide, tri-n-octylphosphine oxide, triphenylphosphine oxide, dimethylethylphosphine oxide, methyldiethylphosphine oxide, diethylpropylphosphine oxide, ethyldipropylphosphine oxide and ethylpropylbutylphosphine oxide.

Preferred phosphine oxides are the straight or branched trialkylphosphine oxides of 1 to 8 carbon atoms having the same $R^1$, $R^2$ and $R^3$ in the formula (I), or triphenylphosphine oxide. More preferred phosphine oxides are selected from the group consisting of trimethylphosphine oxide, triethylphosphine oxide, tri-n-propylphosphine oxide, triisopropylphosphine oxide, tri-sec-butylphosphine oxide, tri-n-butylphosphine oxide, tri-n-hexylphosphine oxide and tri-n octylphosphine oxide.

The organic phosphine oxide can be used singly or in combination as a solvent in the reaction. For example, when triethylphosphine oxide having a melting point of 50° C. and tri-n-butylphosphine oxide having a melting point of 67 to 69° C. are used for the solvent as an equal-amount mixture, the mixture is liquid at room temperature and is easy to handle. The characteristics of the original phosphine oxides do not decrease in the mixture. The mixture exhibits high selectivity of p-hydroxybenzoic acid and a good conversion rate of the raw material equal to the rate attained when each phosphine oxide is used singly.

The alkali salt of phenol used in the process of the present invention may be either a sodium salt or a potassium salt. The potassium salt is favorable in view of selectivity and conversion rate. However, the sodium salt is cheaply available and hence economically advantageous.

When, the carboxylation reaction is carried out in the organic phosphine oxide solvent, high selectivity for p-hydroxybenzoic acid formation can be similarly obtained even though the raw material salt is a salt of heavy metal such as potassium or a salt of light metal such as sodium. Extremely high selectivity can be obtained particularly when the light salt of alkali metal such as sodium is used.

The alkali metal salt of phenol used in the present invention can be prepared by various methods. For example, the sodium salt can be obtained by adding an equivalent amount of sodium hydroxide solution to phenol, evaporating the resulting solution to dryness, and forming a substantially anhydrous salt in a vacuum. More preferably, the sodium salt can be prepared by dissolving phenol in an organic solvent, neutralizing the resulting solution with an aqueous sodium hydroxide solution, and successively distilling off the organic solvent. The alkali metal salt of phenol can be dissolved in the above organic phosphine oxide in high concentrations. For example, the salt is soluble at 100° C. in an amount of 25 parts by weight or more per 100 parts by weight of tri-n-octylphosphine oxide. Hence, the carboxylation reaction is thought to proceed quickly.

The preferred reaction temperature is from 50 to 180° C. A reaction temperature of less than 50° C. decreases the conversion ratio of the alkali metal salt of phenol and unfavorably retards the rate of reaction. On the other hand, a higher reaction temperature improves the conversion ratio of the alkali metal salt of phenol. However, a reaction temperature in excess of 180° C. increases formation of the by-product salicylic acid. When the temperature further exceeds 230° C., formation of dicarboxylic acid by-products such as orthoisophthalic acid becomes pronounced.

No particular restriction is imposed upon the reaction time. The conversion ratio is generally increased by extending the reaction time. The reaction time varies depending upon the raw materials, solvents and reaction temperature. When the reaction temperature is, for example, 80° C., the reaction is generally completed within 12 hours.

Carbon dioxide may be supplied in a stoichiometric amount or more, that is, 1.0 mole or more per mole of the alkali metal salt of phenol.

The reaction is usually carried out by the following two methods. In the first method, the alkali metal salt of raw material is dissolved in the solvent, a stoichiometric amount of carbon dioxide is absorbed and then the carboxylation reaction is carried out by increasing the temperature. In the second method, a solution obtained by dissolving the alkali metal salt in the solvent is heated to the prescribed reaction temperature and then the carboxylation reaction is conducted in combination with blowing carbon dioxide through the solution. Both of the above methods can achieve the object of the present invention, and any other methods may also be employed.

The reaction can be carried out under reduced pressure, in atmospheric pressure or under increased pressure.

When the reaction is particularly carried out under increased pressure, for example, under increased pressure of carbon dioxide, the reaction time can be reduced. A sufficient pressure of carbon dioxide for conducting the reaction is approximately 10 kg/cm²G.

The reaction of the present invention can be carried out either by a batch process or by a continuous process.

In the reaction of the process of the present invention, the conversion ratio of the raw material increases to about 50% and is then maintained at a constant level. The reason is assumed that the reaction proceeds as illustrated in the formula(1) and formula(2):

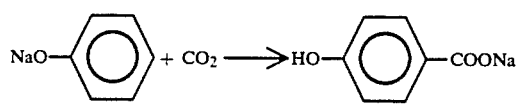

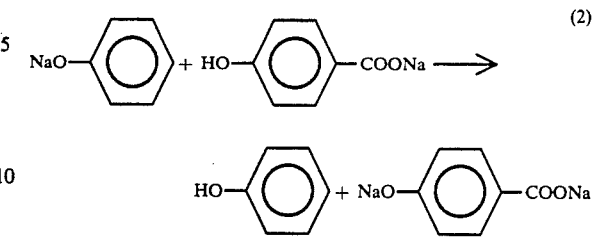

wherein p phydroxybenzoic acid is converted to its sodium salt while the alkali metal salt of phenol is converted to phenol and the reaction is terminated.

In the process of the present invention, by-products are mainly salicylic acid and a small amount of hydroxyisophthalic acid. However, the amounts of these by-products are very small and the aromatic hydroxycarboxylic acid ca be obtained as a main product in high selectivity.

The present invention will hereinafter be illustrated further in detail by way of examples. However, these examples are not to be construed as limiting the scope of the present invention.

The raw materials and products were analyzed by liquid chromatography using silica gel-$C_{18}$ as the packing in the column and acetonitrile-water as eluent.

Example 1

A substantially anhydrous solid of raw material is obtained by dehydrating a solution containing 9.7 g of phenol and 4.4 g of sodium hydroxide.

To a 200$_{ml}$ four-necked glass flask equipped with a stirrer, carbon dioxide inlet tube and reflux condenser, 10 g of anhydrous sodium salt thus-obtained was charged and 70 g of anhydrous triethylphosphine oxide (white solid, melting point 50° C., hereinafter abbreviated as TEPO) which was previously dried with molecular sieve was added as a solvent. The mixture was dissolved at 50° C. with stirring. A homogeneous yellow brown solution was obtained. The solution was maintained at a temperature of 50° C. and carbon dioxide was blown through the solution at atmospheric pressure. After carbon dioxide was sufficiently absorbed, the interior temperature of the reaction vessel was raised to 140° C. over 10 minutes with continued introduction of carbon dioxide, and the reaction was carried out for an hour. After completing the reaction, the reaction mixture was violet and crystals were partly deposited, which phenomena indicated progress of the reaction.

The reaction product was dissolved by adding 140$_{ml}$ of water. The resulting water and TEPO layers were separated and respectively analyzed by liquid chromatography. A phenol conversion ratio of 29.8 % and a p-hydroxybenzoic acid selectivity of 89.5 % were obtained.

Salicylic acid and ortho isophthalic acid were obtained as by-products. Results are illustrated in Table 1.

Example 2

The same procedures as conducted in Example 1 were carried out except that potassium salt was used as a raw material in place of the sodium salt and the reaction temperature was changed to 100° C. Results are illustrated in Table 1.

Example 3

The same procedures as conducted in Example 1 were carried out except that trimethylphosphine oxide (white solid, melting point 140 to 141° C., hereinafter abbreviated as TMPO) was used as a solvent in place of the TEPO, dissolved with stirring in the course of increasing the internal temperature to 140° C., and then the reaction was conducted at 140° C. by blowing carbon dioxide through the solution at atmospheric pressure. Results are illustrated in Table 1.

Example 4

The same procedures as conducted in Example 3 were carried out except that the potassium salt was used as a raw material in place of the sodium salt. Results are illustrated in Table 1.

Comparative Example 1

The same procedures as conducted in Example 1 were carried out except that the reaction was conducted at 200° C. A large amount of salicylic acid was formed as a by-product and selectivity of p-hydroxybenzoic acid decreased. Results are illustrated in Table 1.

Example 5

The same procedures as conducted in Example 1 were carried out except that the potassium salt obtained in Example 2 and tri-n-butylphosphine oxide (white solid, melting point 67 to 69° C., hereinafter abbreviated as TBPO) were mixed, the mixture was dissolved with stirring by increasing the internal temperature of the reaction vessel to 100° C. to obtain a uniform brown solution, and the reaction was conducted at 100° C. for 3 hours by blowing carbon dioxide through the solution at atmospheric pressure. Results are illustrated in Table 1.

Example 6

The same procedures as conducted in Example 5 were carried out except that the sodium salt was used as a raw material in place of the potassium salt and the reaction was conducted at 140° C. Results are illustrated in Table 1.

EXAMPLE 7

The same procedures as conducted in Example 6 were carried out except that tri-n-hexylphosphine oxide (white solid, melting point 34 to 35° C., hereinafter abbreviated as THPO) was used as a solvent in place of the TBPO. Results are illustrated in Table 1.

Comparative Example 3

The same procedures as conducted in Example 7 were carried out except that the reaction temperature was changed to 45° C. and the reaction was conducted for 20 hours. The conversion ratio of the raw material salt was as low as 0.1 % or less. Almost no progress was found in the reaction. Results are illustrated in Table 1.

Example 8

The same procedures as conducted in Example 5 were carried out except that the sodium salt was used as a raw material in place of the potassium salt and tri-n-octylphosphine oxide (white solid, melting point 54 to 56° C., hereinafter abbreviated as TOPO) was used as a solvent in place of the TBPO. Results are illustrated in Table 1.

Comparative Example 4

To a 200$_{ml}$ stainless steel autoclave equipped with a magnetic stirrer and reflux condenser, 140 g of kerosene having a boiling point of 180 to 350° C. and 16.2 g of phenol were charged and phenol was dissolved. Successively, 27 g of an aqueous solution containing 7.3 g of sodium hydroxide was added to neutralize phenol at 60° C. with stirring at atmospheric pressure. Thereafter the mixture was heated to 180 to 220° C. and an azeotropic mixture of kerosene and water was distilled out with stirring. The separated kerosene layer was recycled to the autoclave.

Moisture in the reaction mixture was sufficiently removed by the azeotropic distillation to give sodium salt suspended in kerosene. The suspension was cooled to the room temperature. The interior of the autoclave was replaced with carbon dioxide and further increased in pressure to 5 kg/cm$^2$G with carbon dioxide. Then the autoclave was stirred for an hour to absorb carbon dioxide. The autoclave was charged again with carbon dioxide to a pressure of 5 kg/cm$^2$G and was heated to 180° C. over 30 minutes under vigorous stirring. After reacting at 180° C. for an hour, the reaction mixture was cooled to the room temperature and mixed with 140$_{ml}$ of water. Analysis was carried out as described in Example 1. Results are illustrated in Table 1.

Example 9

The same procedures as conducted in Example 8 were carried out except that triphenylphosphine oxide (melting point 156 to 157° C., hereinafter abbreviated as TPPO) was used as a solvent in place of the TOPO and the reaction temperature was changed to 160° C.

Example 10

To 10 g of the sodium salt prepared in Example 1, 70 g of a solvent obtained by mixing equal amounts by weight of TEPO and TBPO was added to dissolve the sodium salt with stirring at the room temperature. The resulting solution was homogenous and yellow brown colored. Carbon dioxide was blown through the solution at the room temperature under atmospheric pressure to be absorbed sufficiently into the solution. Then the temperature of the solution was raised to 140° C. over 10 minutes under similar introduction of carbon dioxide and the reaction was carried out for 3 hours. Other procedures were conducted as described in Example 1. Results are described in Table 1.

Example 11

The same procedures as conducted in Example 10 were carried out except that an equal-amount mixture by weight of TMPO and TOPO was used as a solvent mixture in place of the TEPO. Results are illustrated in Table 1.

TABLE 1

| Example or Comparative Example | Alkali salt of phenol | Reaction conditions | | | | Conversion ratio (%) | Selectivity[2] | |
|---|---|---|---|---|---|---|---|---|
| | | Solvent[1] | Temperature (°C.) | Time (hr) | Pressure (kg/cm² G) | | POB (%) | SA (%) |
| Ex. 1 | Na-salt | TEPO | 140 | 1 | Atmospheric | 29.8 | 89.5 | 8.8 |
| Ex. 2 | K-salt | TEPO | 100 | 1 | Atmospheric | 31.8 | 95.6 | 3.9 |
| Ex. 3 | Na-salt | TMPO | 140 | 1 | Atmospheric | 38.8 | 94.7 | 2.6 |
| Ex. 4 | K-salt | TMPO | 140 | 1 | Atmospheric | 49.2 | 97.1 | 2.7 |
| Compar. Ex. 1 | Na-salt | TEPO | 200 | 1 | Atmospheric | 42.2 | 62.9 | 33.1 |
| Compar. Ex. 2 | Na-salt | DMF | 140 | 1 | Atmospheric | 31.3 | 65.8 | 32.8 |
| Ex. 5 | K-salt | TBPO | 100 | 3 | Atmospheric | 26.8 | 81.0 | 18.4 |
| Ex. 6 | Na-salt | TBPO | 140 | 3 | Atmospheric | 26.5 | 80.8 | 17.6 |
| Ex. 7 | Na-salt | THPO | 100 | 3 | Atmospheric | 17.0 | 69.2 | 28.4 |
| Compar. Ex. 3 | Na-salt | THPO | 45 | 20 | Atmospheric | 0.1> | 98.0 | 2.0 |
| Ex. 8 | Na-salt | TOPO | 100 | 3 | Atmospheric | 5.7 | 72.6 | 27.4 |
| Ex. 9 | Na-salt | TPPO | 160 | 3 | Atmospheric | 6.3 | 34.1 | 65.6 |
| Compar. Ex. 4 | Na-salt | Kerosene | 180 | 1 | 5.0[3] | 49.0 | 7.6 | 92.4 |
| Ex. 10 | Na-salt | TEPO/TBPO (1/1)[4] | 140 | 3 | Atmospheric | 35.6 | 84.5 | 13.1 |
| Ex. 11 | Na-salt | TMPO/TOPO (1/1)[4] | 140 | 3 | Atmospheric | 36.2 | 86.4 | 11.1 |

Note
[1]TMPO: Trimethylphosphine oxide
TEPO: Triethylphosphine oxide
TBPO: Tri-n-butylphosphine oxide
THPO: Tri-n-hexylphosphine oxide
TOPO: Tri-n-octylphosphine oxide
TPPO: Triphenylphosphine oxide
DMF: N,N-Dimethylformamide
[2]POB: p-Hydroxybenzoic acid
SA: Salicylic acid
[3]Initial pressure
[4]Weight ratio

What is claimed is:

1. A process for the preparation of an aromatic hydroxycarboxylic acid comprising reacting an alkali metal salt of phenol with carbon dioxide in a solvent containing at least one organic phosphine oxide represented by the formula (I):

wherein $R^1$, $R^2$ and $R^3$ are a straight or branched alkyl group having from 1 to 8 carbon atoms or a phenyl gruop and may be same or different from each other.

2. The process of claim 1 wherein the organic phosphine oxide is a compound selected from the group consisting of trimethylphosphine oxide, triethylphosphine oxide, tri-n-propylphosphine oxide, triisopropylphosphine oxide, tri-sec-butylphosphine oxide, tri-n-butylphosphine oxide, tri-n-hexylphosphine oxide, tri-n octylphosphine oxide, dimethylethylphosphine oxide, methyldiethylphosphine oxide, diethylpropylphosphine oxide and ethyldipropylphosphine oxide.

3. The process of claim 1 wherein the organic phosphine oxide is a compound selected from the group consisting of trimethylphosphine oxide, triethylphosphine oxide, tri-n-propylphosphine oxide, triisopropylphosphine oxide, tri-sec-butylphosphine oxide, tri-n-butylphosphine oxide, tri-n-hexylphosphine oxide and tri-n-octylphosphine oxide.

4. The process of claim 1 wherein the organic phosphine oxide is trimethylphosphine oxide.

5. The process of claim 1 wherein the organic phosphine oxide is triethylphosphine oxide.

6. The process of claim 1 wherein the organic phosphine oxide is tri-n-butylphosphine oxide.

7. The process of claim 1 wherein the organic phosphine oxide is tri-n-hexylphosphine oxide.

8. The process of claim 1 wherein the organic phosphine oxide is tri-n-octylphosphine oxide.

9. The process of claim 1 wherein the organic phosphine oxide is triphenylphosphine oxide.

10. The process of claim 1 wherein the alkali metal salt of phenol is a potassium salt of phenol.

11. The process of claim 1 wherein the alkali metal salt of phenol is a sodium salt of phenol.

12. The process of claim 1 wherein the reaction is carried at 50 to 180° C.

UNITED STATES PATENT AND TRADEMARK OFFICE
CERTIFICATE OF CORRECTION

PATENT NO. : 4,950,781

DATED : August 21, 1990

INVENTOR(S) : Takehisa NAKANISHI et al.

It is certified that error appears in the above-identified patent and that said Letters Patent is hereby corrected as shown below:

Column 7
In claim 1, line 59, amend "gruop" to -- group --.

Signed and Sealed this

Sixteenth Day of June, 1992

Attest:

DOUGLAS B. COMER

*Attesting Officer*  Acting Commissioner of Patents and Trademarks

UNITED STATES PATENT AND TRADEMARK OFFICE
CERTIFICATE OF CORRECTION

PATENT NO. : 4,950,781

DATED : August 21, 1990

INVENTOR(S) : Takehisa NAKANISHI et al.

It is certified that error appears in the above-identified patent and that said Letters Patent is hereby corrected as shown below:

In column 1, formula I, amend "R=O" to --P=O--.

In column 2, formula I, amend "R=O" to --P=O--.

In column 7, formula I, amend "R=O" to --P=O--.

Signed and Sealed this

First Day of June, 1993

Attest:

MICHAEL K. KIRK

*Attesting Officer*  *Acting Commissioner of Patents and Trademarks*